United States Patent [19]

Ichihara et al.

[11] Patent Number: 5,405,777
[45] Date of Patent: Apr. 11, 1995

[54] ACETIC ACID ASSIMILATING GENE AND A METHOD FOR PREVENTING ACCUMULATION OF ACETIC ACID IN CULTURE MEDIUM

[75] Inventors: Shigeyuki Ichihara, Kasugai; Takeshi Mizuno, Nagoya, both of Japan

[73] Assignee: Ajinomoto Co., Inc., Tokyo, Japan

[21] Appl. No.: 155,906

[22] Filed: Nov. 23, 1993

Related U.S. Application Data

[63] Continuation of Ser. No. 850,909, Mar. 13, 1992, abandoned.

[30] Foreign Application Priority Data

Aug. 23, 1991 [JP] Japan .................................. 3-212410

[51] Int. Cl.⁶ ..................... C12N 1/21; C12N 15/52; C12N 15/70
[52] U.S. Cl. .......................... 435/252.33; 435/320.1; 536/23.2
[58] Field of Search .................. 435/69.1, 71.1, 170, 435/849, 172.1, 172.3, 243, 252.3, 252.33, 320.1; 536/23.1, 23.2

[56] References Cited

PUBLICATIONS

Shatzman, A. R. Expression, Identification, and Characterization of Recombinant Gene Products in *E. coli* in *Guide to Molecular Cloning Techniques* (Academic Press, San Diego, 1987), pp. 661–673.
Bailey, J. E. Science, vol. 252 (1991), pp. 1668–1675.
Plumbridge, J. A. Molecular Microbiology, vol. 3, No. 4 (1989), pp. 505–515.
Peri, K. G. et al. Biochemistry & Cell Biology, vol. 68 (1990), pp. 123–137.
Nunn, W. D. Genetic & Biochemical Features of Acetate Metabolism in *Escherichia coli* and *Salmonella typhimurium* (Washington, D.C., American Society of Micro), vol. 1, pp. 296–301.
Japanese Abstract No. 3F2a8, Nippon Nogeikagaku Kaishi, vol. 65, No. 3 "A gene derived from *Escherichia coli* related with acetate assimilation", Mar. 1991.

*Primary Examiner*—Richard A. Schwartz
*Assistant Examiner*—Robert A. Hodges
*Attorney, Agent, or Firm*—Oblon, Spivak, McClelland, Maier & Neustadt

[57] ABSTRACT

The gene responsible for the capability of *E. coli* to assimilate acetic acid has been isolated and characterized. Transforming bacteria with this gene enhances the bacteria's ability to assimilate acetic acid and results in a bacteria having improved growth characteristics, particularly on culture media containing glucose as a nutrient.

12 Claims, 20 Drawing Sheets

```
GTGGTTGGTC TGGCCGAAAC ATCATGAACA AAGTCCGGCT GCGGTAACTT TCGTATTCAT    60
CTGCTGAATG CTCTCAGGTG AGGGAAATTT CAACGAAAAA GCCCGAAAAA TGTGCTGTTA   120
ATCACATGCC TAAGTAAAAA TTTGACGACA CGTATTGAAG TGCTTCACCA TAGCCTACAG   180
ATTATTTCGG AGCGCGAAAA TATAGGGAGT ATGCGGTGGT TGCTGAAAAC CAGCCTGGGC   240
ACATTGATCA AATAAAGCAG ACCAACGCGG GCGCGGTTTA TCGCCTGATT GATCAGCTTG   300
GTCCAGTCTC GCGTATCGAT CTTTCCCGTC TGGCGCAACT GGCTCCTGCC AGTATCACTA   360
AAATTGTCCG TGAGATGCTC GAAGCACACC TGGTGCAAGA GCTGGAAATC AAAGAAGCGG   420
GGAACCGTGG CCGTCCCGGCG GTGGGGCTGG TGGTTGAAAC TGAAGCCTGG CACTATCTTT   480
CTCTGCGCAT TAGTCGCGGG GAGATTTTCC TTGCTCTGCG CGATCTGAGC AGCAAACTGG   540
TGGTGGAAGA GTCGCAGGAA CTGGCCGTTAA AAGATGACTT GCCATTGCTG GATCGTATTA   600
TTTCCCATAT CGATCAGTTT TTTATCCGCC ACCAGAAAAA ACTTGAGCGT CTAACTTCGA   660
```

FIG. 1A

```
TTGCCATAAC CTTGCCGGGA ATTATTGATA CGGAAAATGG TATTGTACAT CGCATGCCGT   720
TCTACGAGGA TGTAAAAGAG ATGCCGCTCG CGGAGGCGCT GGAGCAGCAT ACCGGCGTTC   780
CGGTTTATAT TCAGCATGAT ATCAGCGCAT GGACGATGGC AGAGGCCTTG TTTGGTGCCT   840
CACGCGGGGC GCGCGATGTG ATTCAGGTGG TTATCGATCA CAACGTGGGG GCGGGCGTCA   900
TTACCGATGG TCATCTGCTA CACGCAGGCA GCAGTAGTCT CGTGGAAATA GGCCACACAC   960
AGGTCGACCC GTATGGGAAA CGCTGTTATT GCGGGAATCA CGGCTGCCTC GAAACCATCG  1020
CCAGCGTGGA CAGTATTCTT GAGCTGGCAC AGCTGCGTCT TAATCAATCC ATGAGCTCGA  1080
TGTTACATGG ACAACCGTTA ACCGTGGACT CATTGTGTCA GGCGGCATTG CGCGGGCATC  1140
TACTGGCAAA AGACATCATT ACCGGGGTGG GCGCGCATGT CGGGGCGCATT CTTGCCATCA  1200
TGGTGAATTT ATTTAACCCA CAAAAAATAC TGATTGGCTC ACCGTTAAGT AAAGCGGCAG  1260
ATATCCTCTT CCCGGTCATC TCAGACAGCA TCCGTCAGCA GGCCCTTCCT GCGTATAGTC  1320
AGCACATCAG CGTTGAGAGT ACTCAGTTTT CTAACCAGGG CACGATGGCA GGCGCTGCAC  1380
TGGTAAAAGA CGCGATGTAT AACGGTTCTT TGTTGATTCG TCTGTTGCAG GGTTAACATT  1440
TTTTAACTGT TCTACCAAAA TTTGCGCTAT CTCAATTTGG GCCAGGAAAG CATAACTTAG  1500
```

*FIG. 1B*

```
ACTTTCAAGG TTAATTATTT TCCTGGTTTA TATTTGTGAA GCATAACGGT GGAGTTAGTG   1560
ATGCTGAANN NTTTCTTTAT TACCGGTACA GTCACTTATG TAGGGAAAAC GGTGGTTTCC   1620
CGCGCCGATT TC   1632
```

FIG. 1C

```
Met Val Ala Glu Asn Gln Pro Gly His Ile Asp Gln Ile Lys Gln Thr
                     5                  10                  15
Asn Ala Gly Ala Val Tyr Arg Leu Ile Asp Gln Leu Gly Pro Val Ser
                    20                  25                  30
Arg Ile Asp Leu Ser Arg Leu Ala Gln Leu Ala Pro Ala Ser Ile Thr
                    35                  40                  45
Lys Ile Val Arg Glu Met Leu Glu Ala His Leu Val Gln Glu Leu Glu
                    50                  55                  60
Ile Lys Glu Ala Gly Asn Arg Gly Arg Pro Ala Val Gly Leu Val Val
65                  70                  75                  80
Glu Thr Glu Ala Trp His Tyr Leu Ser Leu Arg Ile Ser Arg Gly Glu
                    85                  90                  95
Ile Phe Leu Ala Leu Arg Asp Leu Ser Ser Lys Leu Val Val Glu Glu
                   100                 105                 110
Ser Gln Glu Leu Ala Leu Lys Asp Asp Leu Pro Leu Leu Asp Arg Ile
                   115                 120                 125
```

FIG. 2A

```
Ile Ser His Ile Asp Gln Phe Phe Ile Arg His Gln Lys Lys Leu Glu
                130                 135                 140
Arg Leu Thr Ser Ile Ala Ile Thr Leu Pro Gly Ile Ile Asp Thr Glu
145                 150                 155                 160
Asn Gly Ile Val His Arg Met Pro Phe Tyr Glu Asp Val Lys Glu Met
                165                 170                 175
```

```
Pro Leu Ala Glu Ala Leu Glu Gln His Thr Gly Val Pro Val Tyr Ile
                180                 185                 190
Gln His Asp Ile Ser Ala Trp Thr Met Ala Glu Ala Leu Phe Gly Ala
            195                 200                 205
Ser Arg Gly Ala Arg Asp Val Ile Gln Val Val Ile Asp His Asn Val
        210                 215                 220
Gly Ala Gly Val Ile Thr Asp Gly His Leu Leu His Ala Gly Ser Ser
225                 230                 235                 240
Ser Leu Val Glu Ile Gly His Thr Gln Val Asp Pro Tyr Gly Lys Arg
                245                 250                 255
Cys Tyr Cys Gly Asn His Gly Cys Leu Glu Thr Ile Ala Ser Val Asp
            260                 265                 270
Ser Ile Leu Glu Leu Ala Gln Leu Arg Leu Asn Gln Ser Met Ser Ser
        275                 280                 285
Met Leu His Gly Gln Pro Leu Thr Val Asp Ser Leu Cys Gln Ala Ala
290                 295                 300
Leu Arg Gly Asp Leu Leu Ala Lys Asp Ile Ile Thr Gly Val Gly Ala
```

```
305                     310                 315                 320
His Val Gly Arg Ile Leu Ala Ile Met Val Asn Leu Phe Asn Pro Gln
                    325                 330                 335
Lys Ile Leu Ile Gly Ser Pro Leu Ser Lys Ala Ala Asp Ile Leu Phe
                    340                 345                 350
Pro Val Ile Ser Asp Ser Ile Arg Gln Gln Ala Leu Pro Ala Tyr Ser
                    355                 360                 365
Gln His Ile Ser Val Glu Ser Thr Gln Phe Ser Asn Gln Gly Thr Met
                    370                 375                 380
Ala Gly Ala Ala Leu Val Lys Asp Ala Met Tyr Asn Gly Ser Leu Leu
                    385                 390                 395                 400
Ile Arg Leu Leu Gln Gly
```

FIG. 2D

```
GTGGTTGGTC TGGCCGAAAC ATCATGAACA AAGTCCGGCT GCGGTAACTT TCGTATTCAT    60
CTGCTGAATG CTCTCAGGTG AGGGAAATTT CAACGAAAAA GCCCGAAAAA TGTGCTGTTA   120
ATCACATGCC TAAGTAAAAA TTTGACGACA CGTATTGAAG TGCTTCACCA TAGCCTACAG   180
ATTATTTCGG AGCGCGAAAA TATAGGGAGT ATGCG GTG GTT GCT GAA AAC CAG      233
                                  Met Val Ala Glu Asn Gln
                                                    5

CCT GGG CAC ATT GAT CAA ATA AAG CAG ACC AAC GCG GGC GCG GTT TAT    281
Pro Gly His Ile Asp Gln Ile Lys Gln Thr Asn Ala Gly Ala Val Tyr
            10                  15                  20

CGC CTG ATT GAT CAG CTT GGT CCA GTC TCG CGT ATC GAT CTT TCC CGT    329
Arg Leu Ile Asp Gln Leu Gly Pro Val Ser Arg Ile Asp Leu Ser Arg
        25                  30                  35
```

FIG. 3A

CTG GCG CAA CTG GCT CCT GCC AGT ATC ACT AAA ATT GTC CGT GAG ATG    377
Leu Ala Gln Leu Ala Pro Ala Ser Ile Thr Lys Ile Val Arg Glu Met
         40                  45                  50

CTC GAA GCA CAC CTG GTG CAA GAG CTG GAA ATC AAA GAA GCG GGG AAC    425
Leu Glu Ala His Leu Val Gln Glu Leu Glu Ile Lys Glu Ala Gly Asn
     55                  60                  65                  70

FIG. 3B

```
CGT GGC CGT CCG GCG GGG CTG GTG GTT GAA ACT GAA GCC TGG CAC    473
Arg Gly Arg Pro Ala Val Gly Leu Val Val Glu Thr Glu Ala Trp His
             75                          80                      85

TAT CTT TCT CTG CGC ATT AGT CGC GGG GAG ATT TTC CTT GCT CTG CGC    521
Tyr Leu Ser Leu Arg Ile Ser Arg Gly Glu Ile Phe Leu Ala Leu Arg
             90                          95                     100

GAT CTG AGC AGC AAA CTG GTG GTG GAA GAG TCG CAG GAA CTG GCG TTA    569
Asp Leu Ser Ser Lys Leu Val Val Glu Glu Ser Gln Glu Leu Ala Leu
            105                         110                     115

AAA GAT GAC TTG CCA TTG CTG GAT CGT ATT ATT TCC CAT ATC GAT CAG    617
Lys Asp Asp Leu Pro Leu Leu Asp Arg Ile Ile Ser His Ile Asp Gln
            120                         125                     130

TTT TTT ATC CGC CAC CAG AAA AAA CTT GAG CGT CTA ACT TCG ATT GCC    665
```

FIG.3C

```
Phe Phe Ile Arg His Gln Lys Lys Leu Glu Arg Leu Thr Ser Ile Ala
135                 140                 145                 150

ATA ACC TTG CCG GGA ATT ATT GAT ACG GAA AAT GGT ATT GTA CAT CGC    713
Ile Thr Leu Pro Gly Ile Ile Asp Thr Glu Asn Gly Ile Val His Arg
            155                 160                 165

ATG CCG TTC TAC GAG GAT GTA AAA GAG ATG CCG CTC GCG GAG GCG CTG    761
Met Pro Phe Tyr Glu Asp Val Lys Glu Met Pro Leu Ala Glu Ala Leu
170                 175                 180
```

FIG. 3D

```
GAG CAG CAT ACC GGC GTT CCG GTT TAT ATT CAG CAT GAT ATC AGC GCA    809
Glu Gln His Thr Gly Val Pro Val Tyr Ile Gln His Asp Ile Ser Ala
            185                 190                 195

TGG ACG ATG GCA GAG GCC TTG TTT GGT GCC TCA CGC GGG GCG CGC GAT    857
Trp Thr Met Ala Glu Ala Leu Phe Gly Ala Ser Arg Gly Ala Arg Asp
200                 205                 210

GTG ATT CAG GTG GTT ATC GAT CAC AAC GTG GGG GCG GGC GTC ATT ACC    905
Val Ile Gln Val Val Ile Asp His Asn Val Gly Ala Gly Val Ile Thr
215                 220                 225                 230

GAT GGT CAT CTG CTA CAC GCA GGC AGC AGT CTC GTG GAA ATA GGC        953
Asp Gly His Leu Leu His Ala Gly Ser Ser Leu Val Glu Ile Gly
            235                 240                 245
```

*FIG. 3E*

```
CAC ACA CAG GTC GAC CCG TAT GGG AAA CGC TGT TAT TGC GGG AAT CAC   1001
His Thr Gln Val Asp Pro Tyr Gly Lys Arg Cys Tyr Cys Gly Asn His
        250                     255                     260

GGC TGC CTC GAA ACC ATC GCC AGC GTG GAC AGT ATT CTT GAG CTG GCA   1049
Gly Cys Leu Glu Thr Ile Ala Ser Val Asp Ser Ile Leu Glu Leu Ala
        265                     270                     275

CAG CTG CGT CTT AAT CAA TCC ATG AGC TCG ATG TTA CAT GGA CAA CCG   1097
Gln Leu Arg Leu Asn Gln Ser Met Ser Ser Met Leu His Gly Gln Pro
        280                     285                     290
```

FIG. 3F

```
TTA ACC GTG GAC TCA TTG TGT CAG GCG GCA TTG CGC GGC GAT CTA CTG    1145
Leu Thr Val Asp Ser Leu Cys Gln Ala Ala Leu Arg Gly Asp Leu Leu
295                 300                 305                 310

GCA AAA GAC ATC ATT ACC GGG TGT GGC GCG CAT GTC GGG CGC ATT CTT    1193
Ala Lys Asp Ile Ile Thr Gly Val Gly Ala His Val Gly Arg Ile Leu
        315                 320                 325

GCC ATC ATG GTG AAT TTA TTT AAC CCA CAA AAA ATA CTG ATT GCG TCA    1241
Ala Ile Met Val Asn Leu Phe Asn Pro Gln Lys Ile Leu Ile Gly Ser
330                 335                 340

CCG TTA AGT AAA GCG GCA GAT ATC CTC TTC CCG GTC ATC TCA GAC AGC    1289
Pro Leu Ser Lys Ala Ala Asp Ile Leu Phe Pro Val Ile Ser Asp Ser
345                 350                 355
```

*FIG. 3G*

```
ATC CGT CAG CAG GCC CTT CCT GCG TAT AGT CAG CAC ATC AGC GTT GAG    1337
Ile Arg Gln Gln Ala Leu Pro Ala Tyr Ser Gln His Ile Ser Val Glu
        360                 365                 370

AGT ACT CAG TTT TCT AAC CAG GGC ACG ATG GCA GGC GCT GCA CTG GTA    1385
Ser Thr Gln Phe Ser Asn Gln Gly Thr Met Ala Gly Ala Ala Leu Val
375                 380                 385                 390

AAA GAC GCG ATG TAT AAC GGT TCT TTG TTG ATT CGT CTG TTG CAG GGT    1433
Lys Asp Ala Met Tyr Asn Gly Ser Leu Leu Ile Arg Leu Leu Gln Gly
        395                 400                 405
```

*FIG. 3H*

```
TAA CATT TTTTAACTGT TCTACCAAAA TTTGCGCTAT CTCAATTTGG GCCAGGAAAG   1490

CATAACTTAG ACTTTCAAGG TTAATTATTT TCCTGGTTTA TATTTGTGAA GCATAACGGT  1550

GGAGTTAGTG ATGCTGAANN NTTTCTTTAT TACCGGTACA GTCACTTATG TAGGGAAAAC  1610

GGTGGTTTCC CGCGCCGATT TC   1632
```

FIG. 31

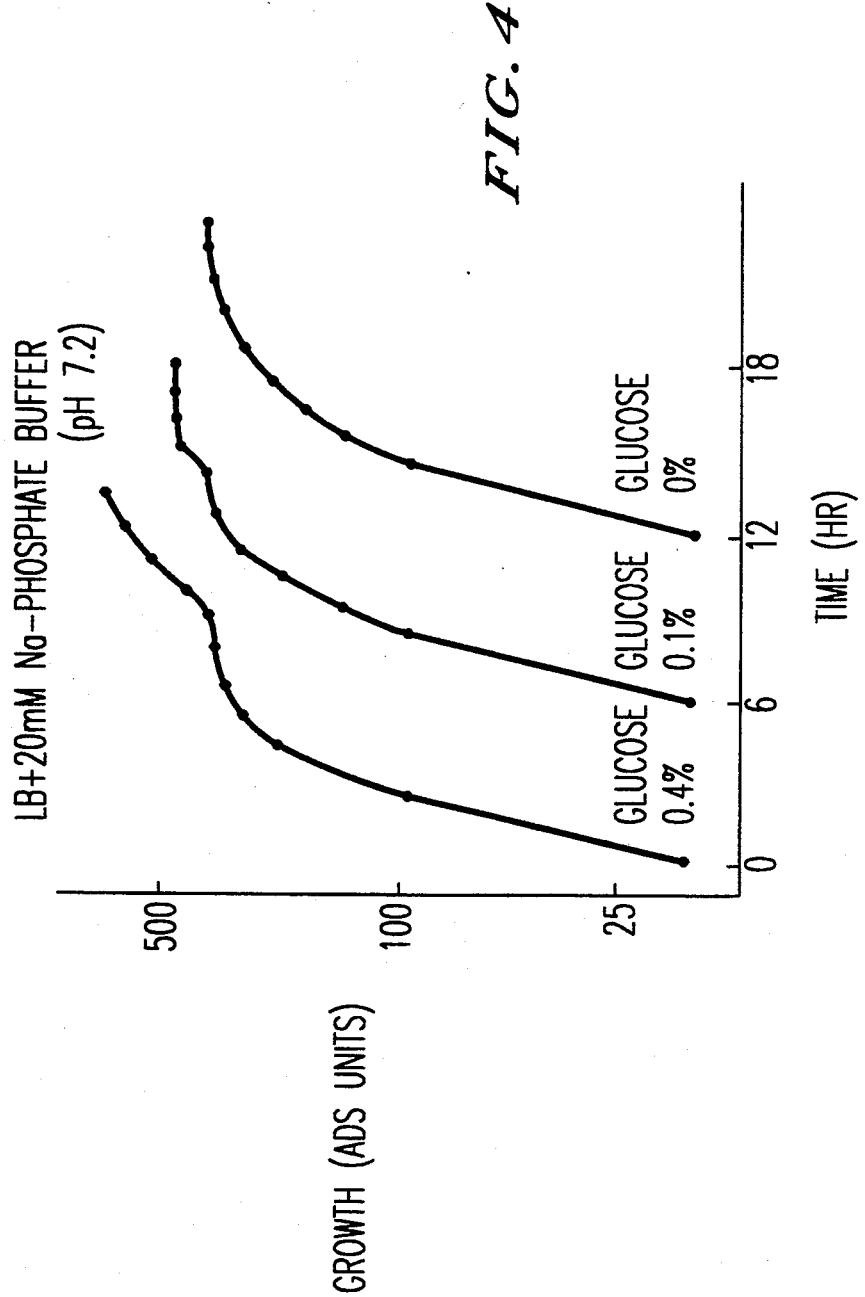

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1632 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GTGGTTGGTC | TGGCCGAAAC | ATCATGAACA | AAGTCCGGCT | GCGGTAACTT | TCGTATTCAT | 60 |
| CTGCTGAATG | CTCTCAGGTG | AGGGAAATTT | CAACGAAAAA | GCCCGAAAAA | TGTGCTGTTA | 120 |
| ATCACATGCC | TAAGTAAAAA | TTTGACGACA | CGTATTGAAG | TGCTTCACCA | TAGCCTACAG | 180 |
| ATTATTTCGG | AGCGCGAAAA | TATAGGGAGT | ATGCGGTGGT | TGCTGAAAAC | CAGCCTGGGC | 240 |
| ACATTGATCA | AATAAAGCAG | ACCAACGCGG | GCGCGGTTTA | TCGCCTGATT | GATCAGCTTG | 300 |
| GTCCAGTCTC | GCGTATCGAT | CTTTCCCGTC | TGGCGCAACT | GGCTCCTGCC | AGTATCACTA | 360 |
| AAATTGTCCG | TGAGATGCTC | GAAGCACACC | TGGTGCAAGA | GCTGGAAATC | AAAGAAGCGG | 420 |
| GGAACCGTGG | CCGTCCGGCG | GTGGGCTGG | TGGTTGAAAC | TGAAGCCTGG | CACTATCTTT | 480 |
| CTCTGCGCAT | TAGTCGCGGG | GAGATTTTCC | TTGCTCTGCG | CGATCTGAGC | AGCAAACTGG | 540 |
| TGGTGGAAGA | GTCGCAGGAA | CTGGCGTTAA | AAGATGACTT | GCCATTGCTG | GATCGTATTA | 600 |
| TTTCCCATAT | CGATCAGTTT | TTTATCCGCC | ACCAGAAAAA | ACTTGAGCGT | CTAACTTCGA | 660 |
| TTGCCATAAC | CTTGCCGGGA | ATTATTGATA | CGGAAAATGG | TATTGTACAT | CGCATGCCGT | 720 |
| TCTACGAGGA | TGTAAAAGAG | ATGCCGCTCG | CGGAGGCGCT | GGAGCAGCAT | ACCGGCGTTC | 780 |
| CGGTTTATAT | TCAGCATGAT | ATCAGCGCAT | GGACGATGGC | AGAGGCCTTG | TYTGGTGCCT | 840 |
| CACGCGGGGC | GCGCGATGTG | ATTCAGGTGG | TTATCGATCA | CAACGTGGGG | GCGGGCGTCA | 900 |
| TTACCGATGG | TCATCTGCTA | CACGCAGGCA | GCAGTAGTCT | CGTGGAAATA | GGCCACACAC | 960 |
| AGGTCGACCC | GTATGGGAAA | CGCTGTTATT | GCGGGAATCA | CGGCTGCCTC | GAAACCATCG | 1020 |
| CCAGCGTGGA | CAGTATTCTT | GAGCTGGCAC | AGCTGCGTCT | TAATCAATCC | ATGAGCTCGA | 1080 |
| TGTTACATGG | ACAACCGTTA | ACCGTGGACT | CATTGTGTCA | GGCGGCATTG | CGCGGCGATC | 1140 |
| TACTGGCAAA | AGACATCATT | ACCGGGGTGG | GCGCGCATGT | CGGGCGCATT | CTTGCCATCA | 1200 |
| TGGTGAATTT | ATTTAACCCA | CAAAAAATAC | TGATTGGCTC | ACCGTTAAGT | AAAGCGGCAG | 1260 |
| ATATCCTCTT | CCCGGTCATC | TCAGACAGCA | TCCGTCAGCA | GGCCCTTCCT | GCGTATAGTC | 1320 |
| AGCACATCAG | CGTTGAGAGT | ACTCAGTTTT | CTAACCAGGG | CACGATGGCA | GGCGCTGCAC | 1380 |
| TGGTAAAAGA | CGCGATGTAT | AACGGTTCTT | TGTTGATTCG | TCTGTTGCAG | GGTTAACATT | 1440 |
| TTTTAACTGT | TCTACCAAAA | TTTGCGCTAT | CTCAATTTGG | GCCAGGAAAG | CATAACTTAG | 1500 |

```
ACTTTCAAGG TTAATTATTT TCCTGGTTTA TATTTGTGAA GCATAACGGT GGAGTTAGTG        1560

ATGCTGAANN NTTTCTTTAT TACCGGTACA GTCACTTATG TAGGGAAAAC GGTGGTTTCC        1620

CGCGCCGATT TC                                                           1632
```

(2) INFORMATION FOR SEQ ID NO:2:

(i) SEQUENCE CHARACTERISTICS:
        (A) LENGTH: 406 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Val Ala Glu Asn Gln Pro Gly His Ile Asp Gln Ile Lys Gln Thr
 1               5                  10                  15

Asn Ala Gly Ala Val Tyr Arg Leu Ile Asp Gln Leu Gly Pro Val Ser
                20                  25                  30

Arg Ile Asp Leu Ser Arg Leu Ala Gln Leu Ala Pro Ala Ser Ile Thr
            35                  40                  45

Lys Ile Val Arg Glu Met Leu Glu Ala His Leu Val Gln Glu Leu Glu
    50                  55                  60

Ile Lys Glu Ala Gly Asn Arg Gly Arg Pro Ala Val Gly Leu Val Val
65                  70                  75                  80

Glu Thr Glu Ala Trp His Tyr Leu Ser Leu Arg Ile Ser Arg Gly Glu
                85                  90                  95

Ile Phe Leu Ala Leu Arg Asp Leu Ser Lys Leu Val Val Glu Glu
                100                 105                 110

Ser Gln Glu Leu Ala Leu Lys Asp Asp Leu Pro Leu Leu Asp Arg Ile
        115                 120                 125

Ile Ser His Ile Asp Gln Phe Phe Ile Arg His Gln Lys Lys Leu Glu
    130                 135                 140

Arg Leu Thr Ser Ile Ala Ile Thr Leu Pro Gly Ile Ile Asp Thr Glu
145                 150                 155                 160

Asn Gly Ile Val His Arg Met Pro Phe Tyr Glu Asp Val Lys Glu Met
                165                 170                 175

Pro Leu Ala Glu Ala Leu Glu Gln His Thr Gly Val Pro Val Tyr Ile
            180                 185                 190

Gln His Asp Ile Ser Ala Trp Thr Met Ala Glu Ala Leu Phe Gly Ala
        195                 200                 205

Ser Arg Gly Ala Arg Asp Val Ile Gln Val Val Ile Asp His Asn Val
    210                 215                 220

Gly Ala Gly Val Ile Thr Asp Gly His Leu Leu His Ala Gly Ser Ser
225                 230                 235                 240

Ser Leu Val Glu Ile Gly His Thr Gln Val Asp Pro Tyr Gly Lys Arg
                245                 250                 255

Cys Tyr Cys Gly Asn His Gly Cys Leu Glu Thr Ile Ala Ser Val Asp
            260                 265                 270

Ser Ile Leu Glu Leu Ala Gln Leu Arg Leu Asn Gln Ser Met Ser Ser
        275                 280                 285

Met Leu His Gly Gln Pro Leu Thr Val Asp Ser Leu Cys Gln Ala Ala
    290                 295                 300

Leu Arg Gly Asp Leu Leu Ala Lys Asp Ile Ile Thr Gly Val Gly Ala
305                 310                 315                 320

His Val Gly Arg Ile Leu Ala Ile Met Val Asn Leu Phe Asn Pro Gln
                325                 330                 335
```

|     |     |     |     |     |     |     |     |     |     |     |     |     |     |
| --- | --- | --- | --- | --- | --- | --- | --- | --- | --- | --- | --- | --- | --- |
| Lys | Ile | Leu | Ile     | Gly | Ser | Pro | Leu | Ser     | Lys | Ala | Ala | Asp | Ile     | Leu | Phe |
|     |     |     | 340 |     |     |     |     | 345 |     |     |     |     | 350 |     |     |
| Pro | Val | Ile | Ser     | Asp | Ser | Ile | Arg | Gln     | Gln | Ala | Leu | Pro | Ala     | Tyr | Ser |
|     |     |     | 355 |     |     |     |     | 360 |     |     |     |     | 365 |     |     |
| Gln | His | Ile | Ser     | Val | Glu | Ser | Thr | Gln     | Phe | Ser | Asn | Gln | Gly     | Thr | Met |
|     |     |     | 370 |     |     |     |     | 375 |     |     |     |     | 380 |     |     |
| Ala | Gly | Ala | Ala     | Leu | Val | Lys | Asp | Ala     | Met | Tyr | Asn | Gly | Ser     | Leu | Leu |
| 385 |     |     |         |     | 390 |     |     |         |     | 395 |     |     |         |     | 400 |
| Ile | Arg | Leu | Leu     | Gln | Gly |     |     |         |     |     |     |     |         |     |     |
|     |     |     |         | 405 |     |     |     |         |     |     |     |     |         |     |     |

( 2 ) INFORMATION FOR SEQ ID NO:3:

( i ) SEQUENCE CHARACTERISTICS:
        ( A ) LENGTH: 1627 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

| | | | | | |
|---|---|---|---|---|---|
| GTGGTTGGTC | TGGCCGAAAC | ATCATGAACA | AAGTCCGGCT | GCGGTAACTT | TCGTATTCAT | 60 |
| CTGCTGAATG | CTCTCAGGTG | AGGGAAATTT | CAACGAAAAA | GCCCGAAAAA | TTGCTGTTAA | 120 |
| TCACATGCCT | AAGTAAAAAT | TTGACGACAC | GTATTGAAGT | GCTTCACCAT | AGCCTACAGA | 180 |
| TTATTTCGGA | GCGCGAAAAT | ATAGGGAGTA | TGCGGTGGTT | GCTGAAAACC | AGCCTGGGCA | 240 |
| CATTGATCAA | ATAAAGCAGA | CCAACGCGGG | CGCGGTTTAT | CGCCTGATTG | ATCAGCTTGG | 300 |
| TCCAGTCTCG | CGTATCGATC | TTTCCCGTCT | GGCGCAACTG | GCTCCTGCCA | GTATCACTAA | 360 |
| AATTGTCCGT | GAGATGCTCG | AAGCACACCT | GGTGCAAGAG | CTGGAAATCA | AGAAGCGGG | 420 |
| GAACCGTGGC | CGTCCGGCGG | TGGGGCTGGT | GGTTGAAACT | GAAGCCTGGC | ACTATCTTTC | 480 |
| TCTGCGCATT | AGTCGCGGGG | AGATTTTCCT | TGCTCTGCGC | GATCTGAGCA | GCAAACTGGT | 540 |
| GGTGGAAGAG | TCGCAGGAAC | TGGCGTTAAA | AGATGACTTG | CCATTGCTGG | ATCGTATTAT | 600 |
| TTCCCATATC | GATCAGTTTT | TTATCCGCCA | CCAGAAAAAA | CTTGAGCGTC | TAACTTCGAT | 660 |
| TGCCATAACC | TTGCCGGGAA | TTATTGATAC | GGAAAATGGT | ATTGTACATC | GCATGCCGTT | 720 |
| CTACGAGGAT | GTAAAAGAGA | TGCCGCTCGC | GGAGGCGCTG | GAGCAGCATA | CCGGCGTTCC | 780 |
| GGTTTATATT | CAGCATGATA | TCAGCGCATG | GACGATGGCA | GAGGCCTTGT | TTGGTGCCTC | 840 |
| ACGCGGGGCG | CGCGATGTGA | TTCAGGTGGT | TATCGATCAC | AACGTGGGGG | CGGGCGTCAT | 900 |
| TACCGATGGT | CATCTGCTAC | ACGCAGGCAG | CAGTAGTCTC | GTGGAAATAG | CCACACACA | 960 |
| GGTCGACCCG | TATGGGAAAC | GCTGTTATTG | CGGGAATCAC | GGCTGCCTCG | AAACCATCGC | 1020 |
| CAGCGTGGAC | AGTATTCTTG | AGCTGGCACA | GCTGCGTCTT | AATCAATCCA | TGAGCTCGAT | 1080 |
| GTTACATGGA | CAACCGTTAA | CCGTGGACTC | ATTGTGTCAG | GCGGCATTGC | GCGGCGATCT | 1140 |
| ACTGGCAAAA | GACATCATTA | CCGGGGTGGG | CGCGCATGTC | GGGCGCATTC | TTGCCATCAT | 1200 |
| GGTGAATTTA | TTTAACCCAC | AAAAAATACT | GATTGGCTCA | CCGTTAAGTA | AAGCGGCAGA | 1260 |
| TATCCTCTTC | CCGGTCATCT | CAGACAGCAT | CCGTCAGCAG | GCCCTTCCTG | CGTATAGTCA | 1320 |
| GCACATCAGC | GTTGAGAGTA | CTCAGTTTTC | TAACCAGGGC | ACGATGGCAG | GCGCTGCACT | 1380 |
| GGTAAAAGAC | GCGATGTATA | ACGGTTCTTT | GTTGATTCGT | CTGTTGCAGG | GTTAACATTT | 1440 |
| TTTAACTGTT | CTACCAAAAT | TTGCGCTATC | TCAATTTGGG | CCAGGAAACA | TAACTTAGAC | 1500 |
| TTTCAAGGTT | AATTATTTTC | CTGGTTTATA | TTTGTGAAGC | ATAACGGTGG | AGTTAGTGAT | 1560 |
| GCTGAATTTC | TTTATTACCG | GTACAGTCAC | TTATGTAGGG | AAAACGGTGG | TTTCCCGCGC | 1620 |

CGATTTC                                                                                                1627

ACETIC ACID ASSIMILATING GENE AND A METHOD FOR PREVENTING ACCUMULATION OF ACETIC ACID IN CULTURE MEDIUM

This application is a continuation of application Ser. No. 07/850,909, filed on Mar. 3, 1992, now abandoned.

BACKGROUND OF THE INVENTION

1. Field of the Invention

The present invention relates to an acetic acid assimilating gene of *Escherichia coli*, the polypeptide encoded by this gene, recombinant plasmids containing this gene, bacteria which have been transformed with such plasmids, and a method of producing a product by culturing such bacteria.

2. Discussion of the Background

When glucose is added to the medium for liquid culture of *E. coli*, acetic acid is released from the cells which assimilate (metabolize) the glucose, so that the pH value of the medium is lowered with the passage of the culture time and the growth of the cells, which is well known. Lowering of the pH value of the medium inhibits growth of the cells, which, therefore, is a serious problem in the production of products such as amino acids by fermentation.

Some attempts to overcome the problem by improvement of the cells to be cultured have heretofore been made by some groups. For instance, Bauer et al. utilized a strain having a deletion in the route by which acetic acid is produced in the production of IL-2 by fermentation, by employing a mutant having a defective phosphotransacetylase. When culturing this strain, acetic acid was not accumulated in the medium, and the growth of the cells was not inhibited (Keith A. B. et al., *Appl. Environ. Microbiol.*, 56:1296, 1990). Matsuyama et al. succeeded in isolating a gene encoding an acetate kinase (ackA) which participates in the route of producing acetic acid by *E. coli* (Asahi M. et al., *J. Bacteriol.*, 171:577, 1989).

However, there remains a need for alternative methods for improving the culture of *E. coli* when using glucose as a nutrient.

SUMMARY OF THE INVENTION

Accordingly, it is one object of the present invention to provide a solution to the problem of how to prevent the inhibition of the growth of cells resulting from the accumulation of acetic acid in the medium during the production of a substance by fermentation.

It is another object of the present invention to provide a novel gene which imparts the ability to assimilate (metabolize) acetic acid to a bacteria.

It is another object of the present invention to provide a novel polypeptide encoded by such a gene.

It is another object of the present invention to provide novel plasmids which contain such a gene.

It is another object of the present invention to provide novel bacteria which have been transformed with such a plasmid.

It is another object of the present invention to provide novel bacteria which contain a heterologous gene which imparts the ability to assimilate acetic acid.

It is another object of the present invention to provide a method for producing a biological product by culturing a bacteria capable of producing the product and which contains a heterologous gene which imparts the ability to assimilate acetic acid.

These and other objects, which will become apparent during the course of the following detailed description, have been achieved by the inventors discovery of a gene in *E. coli* which gene is considered to participate in *E. coli*'s assimilation of acetic acid. The protein encoded by the gene is referred to as acetate P (AceP) hereinafter. On the basis of the finding, the inventors have succeeded in isolating the gene and analyzing the structure of the gene and thus have completed the present invention. Thus, by transforming a bacteria with a plasmid or other suitable vector containing such a gene, it is possible to impart the ability to assimilate (metabolize) acetic acid to the bacteria and improve the production of a biological product by fermentation of the bacteria when using glucose as a nutrient.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A, 1B and 1C show the DNA sequence (SEQ ID No:1) of a preferred DNA fragment according to the present invention;

FIGS. 2A, 2B, 2C, and 2D show the amino acid sequence (SEQ ID NO:2) of the polypeptide encoded by the gene of the present invention;

FIGS. 3A, 3B, 3C, 3D, 3E, 3F, 3G, 3H, and 3I show both the DNA sequence (SEQ ID NO:1) of a preferred DNA fragment of the present invention and the amino acid sequence (SEQ ID NO:2) of the polypeptide encoded by the gene of the present invention;

FIG. 4 shows a growth curve for the culture of *E. coli* JM103 strain in a glucose-added L-medium. The medium was maintained at pH 7.2 using a sodium phosphate buffer. Only in the medium with glucose added thereto was the two-step propagation of the cells observed.

DETAILED DESCRIPTION OF THE PREFERRED EMBODIMENTS

Thus, in one embodiment, the present invention relates to an acetic acid assimilating gene (AceP) which encodes a polypeptide having the amino acid sequence of SEQ ID NO:2 of the Sequence Listing and shown in FIG. 2. The present invention will now be explained in detail hereunder.

When *E. coli* is cultured with glucose as a carbon source, acetic acid is formed as a decomposition product (metabolic product) and is extracellularly secreted out of the cells, whereby the pH value of the culture medium is lowered and the growth of the cells is inhibited, as is well known. If a buffer is added to the medium to maintain the pH value of the medium at a constant value, *E. coli* grows in the glucose-added medium with a two-step propagation profile, as shown in FIG. 4. This result is similar to the two-step propagation profile by *E. coli* which is often seen in culture of it in a medium containing both lactose and glucose. The present inventors considered that the phenomenon could reflect the fact that the *E. coli* which has consumed the glucose in the medium would again grow by assimilating the acetic acid secreted in the medium as the next carbon source. That is to say, the inventors considered that *E. coli* could have gene(s) which participate in the assimilation of acetic acid, which would be induced and expressed after the depletion of glucose and accumulation of acetic acid. Such gene production induced by acetic acid has not been previously reported. The present inventors further considered that analysis of any such genes could result in the discovery of new genes which participate in the assimilation of acetic acid and the acetic acid assimilating mechanism in *E. coli* or impart or enhance the ability to assimilate acetic acid to bacteria, such as *E. coli*, which are unable to or only poorly assimilate acetic acid. After the analysis, the inventors succeeded in the isolation of the desired genes and the determination of the structure of the same.

Figure 5:
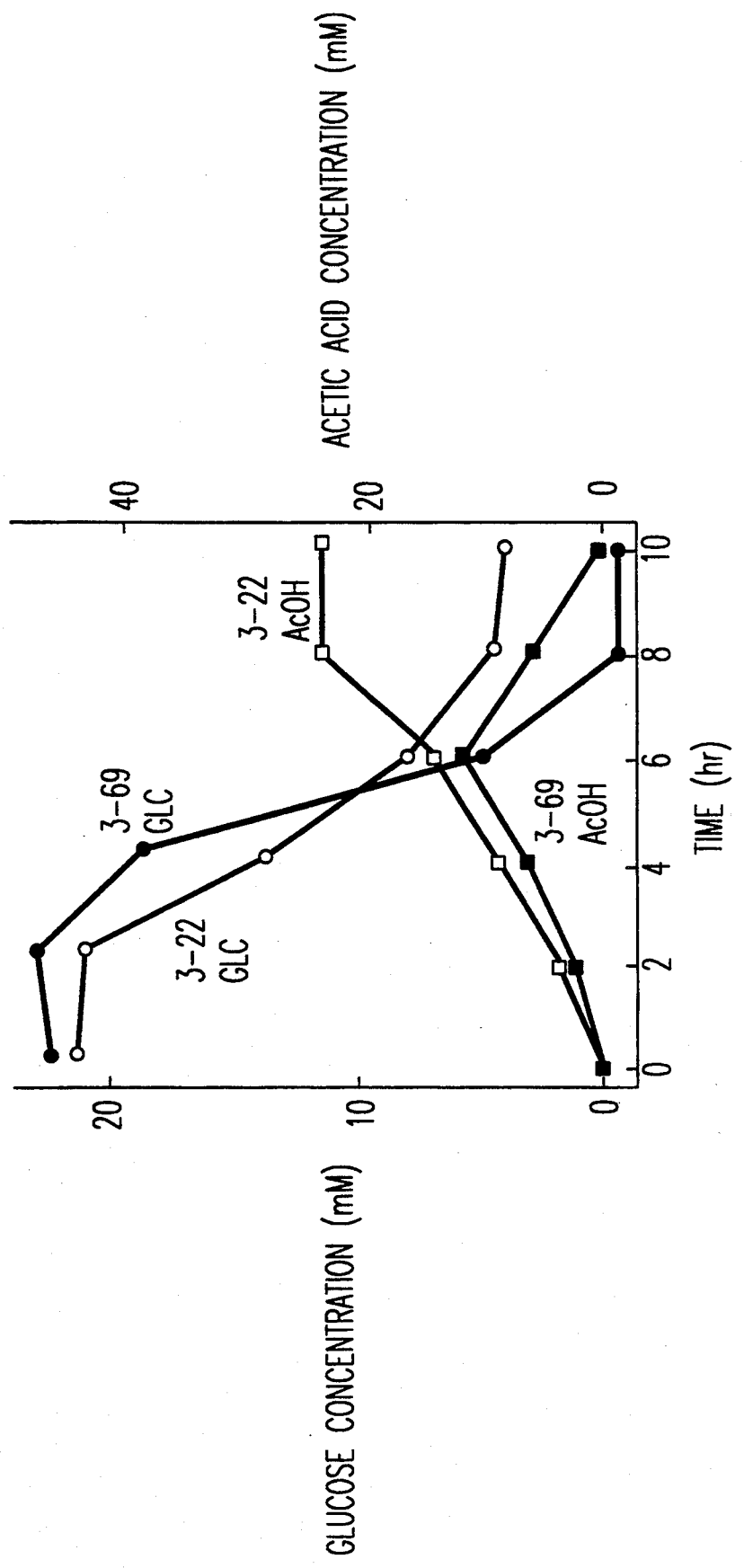
FIG. 5 shows the comparison between the 3-69 strain obtained by shot-gun cloning and the 3-22 strain transformed with vector only, with respect to acetic acid assimilating capacity. A glucose-added L-medium was used for culturing both strains. The concentrations of glucose (○, 3-22 culture; ●, 3-69 culture) and that of acetic acid (□, 3-22 culture; ■, 3-69 culture) in the medium were measured in cultures of both 3-69 strain and 3-22 strain as a function of time, and the results are plotted in the graphs.
Figure 6:
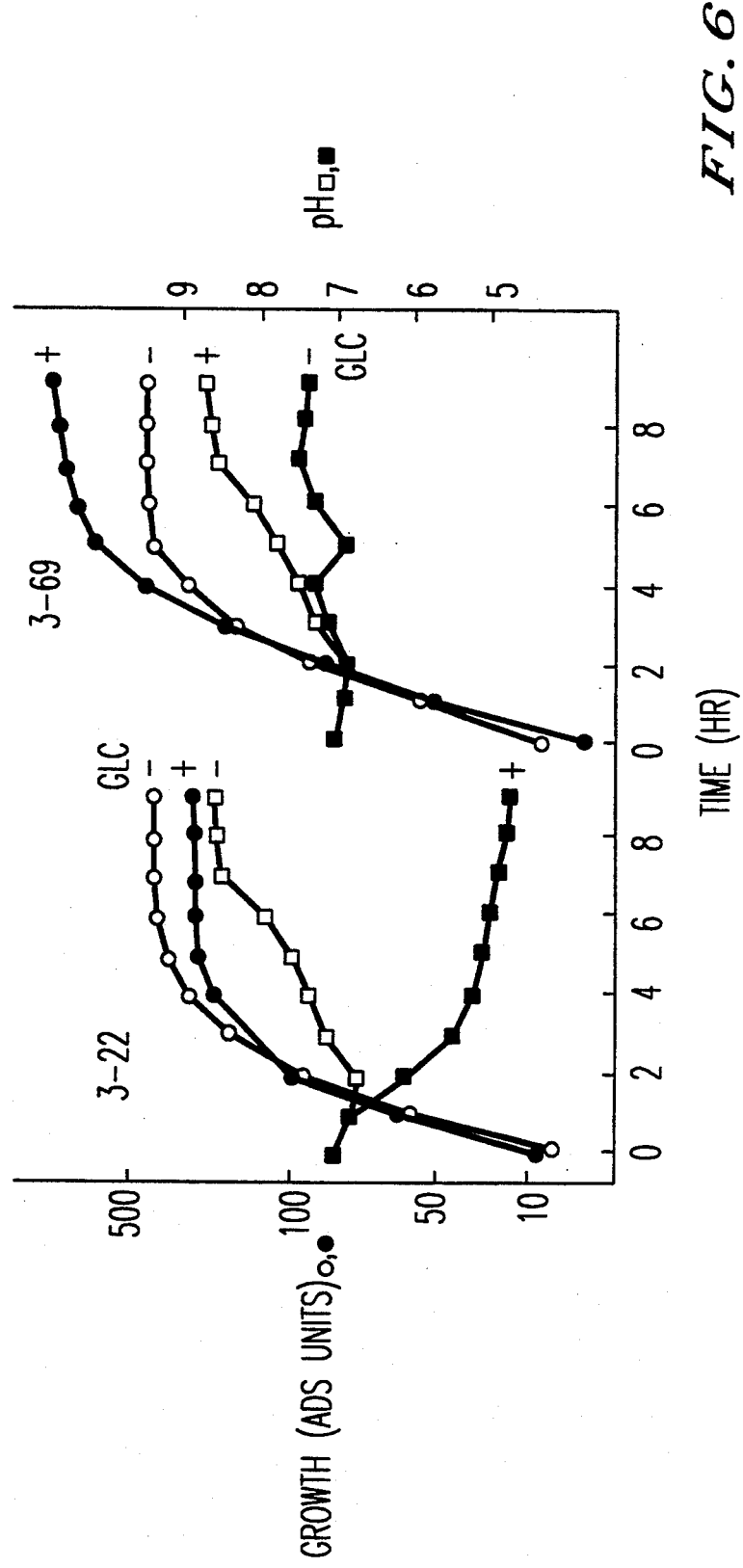
FIG. 6 shows the comparison of the growth of 3-69 strain as obtained by shot-gun cloning and that of 3-22 strain transformed with vector only. A glucose-added L-medium and a glucose-free L-medium were used when culturing both strains. The four curves on the left side of the FIGURE represents the results for 3-22, and the four curves of the right side of the Figure represent the results for 3-69. The graphs show the time-dependent variation of pH values ■, glucose-containing medium; □, glucose-free medium) of the medium along with the growth curves ●, glucose-containing medium; ○, glucose-free medium).

As a method of isolating the genes, a plasmid vector was used to form a gene library of *E. coli* chromosomes and the obtained recombinant DNA mixture was introduced into *E. coli*. Then, the resulting transformant cells were inoculated on a glucose-added agar L medium. These cells were incubated at 37° C., whereupon a transformant strain forming large colonies whose growth is not inhibited by the accumulation of acetic acid in the medium was obtained. In fact, even though incubated in a glucose-added medium, culturing the transformant strain (hereinafter referred to as "3-69 strain") did not result in the accumulation of acetic acid in the medium and a lowering of the pH value of the medium resulting from the accumulation of acetic acid, as shown in FIGS. 5 and 6. As compared with a transformant 3-22 strain which was transformed only with the vector plasmid DNA, the growth of the 3-69 strain in the medium was also better. In addition, the growth of the 3-69 strain in an acetic acid-containing medium was significantly greater than that of the 3-22 strain. From these facts, the recombinant DNA in the transformant 3-69 strain was presumed to have a gene involved in the assimilation of acetic acid (hereinafter referred to as "acetate P gene, or AceP") as inserted thereinto, and isolation of the gene and determination of the structure of the same were conducted as described below.

First, the preparation of DNA containing the acetate P gene will be described. A wild-type *E. coli* such as *E. coli* W3110 strain is cultured to obtain a culture product. In culturing the microorganism, the use of a liquid culture method is preferred over an ordinary solid culture method, though both of them may well be employed. The medium to be used for culturing them may be, for example, one that contains one or more nitrogen sources of yeast extract, peptone, meat broth, corn steep liquor and soybean or wheat-leached liquid, one or more inorganic salts of potassium primary phosphate, potassium secondary phosphate, magnesium sulfate, sodium chloride, magnesium chloride, ferric chloride, ferric sulfate and manganese sulfate, and optionally other additives of raw materials of saccharides and vitamins. The initial pH value of the medium is desired to within the range between 7 and 8. Cultivation of the microorganisms is effected at a temperature of 30° to 42° C., preferably at about 37° C., for 4 to 24 hours by aerial stirring deep culture, shaking culture or static culture. The cultured product thus obtained is subjected to centrifugation, for example, at 3,000 r.p.m. for 5 minutes to obtain cells of *E. coli* W3110 strain.

From these cells, a chromosomal DNA is obtained, for example, by the method of Saito & Miura (*Biochem. Bioshys. Acta.*, 72:819, 1963) or K. S. Kirby (*Biochem. J.*, 64:405, 1956).

Next, the chromosomal DNA is digested with a restriction endonuclease such as Sau 3AI, at a temperature of 30° C. or higher, preferably 37° C., at an enzyme concentration of from 1 to 10 units/ml for varying periods of time of from 1 minute to 2 hours, for partial digestion of it into a mixture of various chromosomal DNA fragments. On the other hand, as a vector DNA for use in the present invention, a plasmid vector DNA, such as pUC19, is preferred. The vector DNA is completely digested with a restriction endonuclease Bam HI, which gives a cohesive end having the same terminal base sequence as that afforded by the restriction endonuclease Sau 3AI which was used in cutting the chromosomal DNA, at a temperature of 30° C. or higher, at an enzyme concentration of from 10 to 10,000 units/ml for one hour or more, preferably from 1 to 3 hours, to obtain cut and cleaved DNA fragments. Next, the mixture containing DNA fragments containing the acetate P gene derived from *E. coli* W3110 strain, thus obtained as mentioned above, and the cleaved vector DNA fragments are mixed, then the resulting mixture is treated with a DNA ligase, preferably T4 DNA ligase, at a temperature of from 4° to 16° C. at an enzyme concentration of from 1 to 100 units/ml for one hour or more, preferably from 8 to 24 hours, to thereby obtain a recombinant DNA.

Using the recombinant DNA, for example, *E. coli* K-12 strain, preferably JM103 strain, is transformed to obtain a transformant strain. The transformation may be effected in accordance with the method of D. M. Morrison (*Methods in Enzymology*, 68:326, 1979). Then, the resulting transformant cells were inoculated on a glucose-added agar L medium. These cells were incubated at 37° C., whereupon a transformant strain forming large colonies whose growth is not inhibited by the accumulation of acetic acid in the medium was obtained. From the transformed cells, can be obtained *E. coli* having a recombinant DNA fragment constructed by inserting an acetate P gene-containing DNA into a vector DNA, for example, by the method of P. Guerry et al (*J. Bacteriol.*, 116:1064, 1973) or D. B. Clewel (*J. Bacteriol.*, 110:667, 1972). From these *E. coli* cells, an acetate P gene-containing recombinant DNA fragment can be recovered.

The recovered passenger DNA is deleted from both the 3' side and the 5' side to various degrees to form a shortened DNA fragment. For the formation of such a shortened DNA, for example, a method utilizing of Mung Bean Nuclease or Exonuclease III can be employed. The shortened DNA is linked to the vector to again transform *E. coli*. With the indication that the resulting transformant has the capacity of forming large colonies on a glucose-containing L-Broth agar medium, restriction and determination of the region of the gene may be effected.

Using the transformant DNA containing the shortened DNA with which the restriction and determination of the gene was effected as mentioned above, analysis of all the base sequence of the part which is considered to be the acetate P gene is conducted in the manner as shown in Example 8 to follow hereinafter, and thereafter the amino acid sequence of the polypeptide encoded by the gene having the base sequence is deduced (as shown in the SEQ ID NO:2 and FIG. 2). The gene encoding the thus established amino acid sequence is the acetate P gene of the present invention. *Escherichia coli* AJ12642 harboring a plasmid having the most shortened DNA with all the region of the acetate P gene (hereinafter referred to as pACEP-1) was deposited with the Fermentation Research Institute of Japan, Agency of Industrial Science and Technology, Ministry of International Trade and Industry, 1-3, Higashi 1-Chome, Yatabe-Machi, Tsukuba-Gun, Ibaraki-Ken 305, Japan, and assigned the Deposit No. FERM BP-3781.

In another embodiment, the present invention relates to the polypeptide which is encoded by the present gene. This polypeptide may be used to augment a bacterium's ability to assimilate acetic acid by adding the polypeptide directly to the culture medium of the bacteria. The polypeptide may be prepared by either solid state synthesis or by transforming a bacteria with a plasmid containing the present gene and isolating the polypeptide produced.

In a further embodiment, the present invention relates to a plasmid which contains the present gene. As noted above, pUC19 is the preferred plasmid in which to insert the present gene. However, any other plasmid suitable for transforming a bacteria, such as *E. coli*, may serve as the plasmid in which the present gene is inserted. Examples of such plasmids include: pUC19, pUC119, pUC18, pUC118, pBR322, pACYC184, pACYC177, RSF1010, pMW119, pHSG298, and pHSG396. It is to be understood that the present plasmid may contain, in addition to the present gene, another gene which encodes for the production of a product such as insulin, IL-2, EPO, IL-6, etc. The production of such plasmids may be accomplished with conventional techniques.

In another embodiment, the present invention relates to strains of bacteria which have been transformed with one of the present plasmids and/or contain a heterologous DNA sequence containing the present gene. Preferably, the bacteria is a strain of *E. coli*, but other genera and species, such as those belonging to the genera *Serratia* and *Salmonella*, may serve as the host. Examples of preferred strains of *E. coli* include: *E. Coli* HB101, *E. Coli* JM109, *E. Coli* DHα5, and *E. coli* W3110. It should be understood that the present bacteria may be transformed with another plasmid, in addition to one of the present plasmids, and that the other plasmid may contain another gene which encodes for a biologically useful product, such as insulin, IL-2, EPO, IL-6, etc. The production of the present microorganisms may be carried out by conventional transformation techniques which are well within the abilities of one skilled in the art.

The present invention also relates to a method for preparing a biological product by fermentation involving culturing a transformed bacteria which is capable of producing the biological product and contains a heterologous DNA sequence encoding the present gene. As noted above the gene encoding the biological product and the present gene may be contained on the same plasmid or may be contained on different plasmids. Examples of such biological products include insulin, IL-2, EPO, IL-6, and amino acids, such as naturally occurring L-α-amino acids. The preferred strain for producing IL-2 is *E. coli* HB101, the preferred strain for producing amino acids is *E. coli* W3110, and the preferred strain for producing IL-6 is *E. coli* HB101. The culturing of the bacteria for production of the biological product and the isolation of the biological product may be carried out in accordance with conventional techniques known in the art.

Having generally described the present invention, a further understanding can be obtained by reference to certain specific examples which are provided herein for purposes of illustration only and are not intended to be limiting unless otherwise specified.

EXAMPLES Example 1

Preparation of Chromosomal DNA of *E. coli* W3110 Strain:

*E. coli* W3110 strain was inoculated in 100 ml of a T-Y medium [1% Bacto-trypton (Difco), 0.5% Bacto-yeast extract (Difco), 0.5% NaCl pH 7.2] and incubated at a temperature of 37° C. for 8 hours to obtain a culture product. The resulting culture product was subjected to ordinary centrifugation at 3,000 r.p.m. for 15 minutes to obtain 0.5 g of wet cells. From the cells was obtained a chromosomal DNA by the method of Saito & Miura (*Biochem. Biophys. Acta,* 72:619, 1963). Next, 60 μg of the chromosomal DNA and 3 units of restriction endonuclease Sau 3AI were mixed in 10 mM tris-hydrochloride buffer (containing 50 mM NaCl 10 mM MgSO$_4$ and 1 Mm dithiothreitol; pH 7.4) and were reacted at a temperature of 37° C. for 30 minutes. After the reaction, the reaction mixture was subjected to ordinary phenol extraction and ethanol precipitation to obtain 50 μg of chromosomal DNA fragments of *E. coli* W3110 strain as digested with Sau 3AI.

Example 2

Formation of Gene Library of *E. coli* W3110 Strain with Plasmid Vector DNA:

20 μg of plasmid vector DNA (pUC19) and 200 units of restriction endonuclease BamHI were blended in 50 mM tris-hydrochloride buffer (containing 100 mM NaCl and 10 mM magnesium sulfate; pH 7.4) and reacted at a temperature of 37° C. for 2 hours to obtain a digested liquid, which was then subjected to ordinary phenol extraction and ethanol precipitation. Next, for preventing re-ligation of the plasmid vector-derived DNA fragments, the DNA fragments were dephosphorylated by treatment with a bacterial alkaline phosphatase in accordance with the method described in Maniatis et al, *Molecular Cloning*, Cold Spring Harbor Laboratory, p. 133 (1982). Then, they were again subjected to ordinary phenol extraction and ethanol precipitation.

1 μg of the pUC19 as digested with BamHI, 1 μg of the chromosomal DNA fragments of E. coli W3110 strain as digested with Sau 3AI, as obtained in Example 1, and 2 units of T4 DNA ligase (produced by Takara Shuzo Co., Japan) were added to 66 mM tris-hydrochloride buffer (pH 7.5) containing 66 mM magnesium chloride, 10 mM dithiothreitol and 10 mM ATP and were reacted at a temperature of 16° C. for 16 hours so that the DNA fragments were ligated to each other. Next, E. coli JM103 strain was transformed with the DNA mixture by a conventional method, and the resulting transformant cells were spread on an L-agar medium containing 100 μg/ml of ampicillin to obtain about 5,000 colonies to be a gene library.

Example 3

Recovery of Recombinant DNA from Gene Library:

From the above-mentioned about 5,000 colonies, a recombinant DNA was recovered. Briefly, the 5,000 colonies were divided into 50 batches each having 100 colonies of them, from which the desired DNA was recovered. Recovery of the DNA was effected in accordance with the above-mentioned method of Guerry et al.

Example 4

Transformation of E. Coli JM103 Strain:

The recombinant DNA mixture as divided into 50 batches was introduced into JM103 strain in accordance with the above-mentioned conventional transformation method. The resulting recombinant cells were plated on a glucose-added agar L-medium and incubated thereon by static culture at 37° C. From them, one strain, forming larger colonies than the others, was selected and was named 3-69 strain, which contained a recombinant DNA fragment containing AceP. The strain was free from inhibition of the growth even under the pH value lowered condition in a glucose-added L-liquid medium (see FIG. 6).

Example 5

Detection of Acetic Acid Assimilating Capacity of Strain with Multiple Copies of Acetate P Gene:

In order to ascertain the fact that the acetate P gene as obtained in the present invention codes for a protein participating in the assimilation of acetic acid, 3-69 strain (having aceP as multiple copies) and 3-22 strain (having pUC19) were compared with each other on an LB/glucose medium with respect to consumption of glucose and accumulation of acetic acid in the medium. The results are shown in FIG. 5. From these results, it is understood that the 3-22 strain accumulated acetic acid with its consumption of glucose like the wild strain, while the 3-69 strain consumed acetic acid as a carbon source after glucose was depleted. From these results, it was ascertained that the acetic acid assimilating capacity of the transformant E. coli was elevated due to the presence of AceP as multiple copies therein.

Example 6

Formation of Shortened DNA:

The recombinant DNA was recovered from the 3-69 strain and a shortened DNA fragment was formed for the purpose of effecting restriction of the gene region and the determination of the base sequence thereof. For forming the shortened DNA, a deletion kit produced by Takara Shuzo Co. of Japan was used in accordance with the producer's instruction. Briefly, E. coli was again transformed with the shortened DNA, and the region of the gene was defined with the indication that the resulting transformant has a capacity of forming large colonies on a glucose-containing L-agar medium. Finally, the necessary region of the gene was defined to about 1600 bp. The smallest DNA fragment containing the region (1.9 kb) was inserted into pUC19, and the resulting plasmid was called pACEP-1. Various shortened DNA fragments in the restricted region were used for determination of the base sequence.

Example 7

Preparation of Various Shortened DNA fragments:

E. coli JM103 strains containing various shortened DNA fragments as obtained above were pre-cultured in 1 l of a medium comprising 1% of trypton, 0.5% of yeast extract and 10.5% of NaCl at a temperature of 37° C. for 24 hours, and 20 ml of the resulting culture liquid was inoculated on 1 l of the same medium and incubated at a temperature of 37° C. for 3 hours. Then, 0.2 g of chloramphenicol was added to the medium, which was further incubated at the same temperature for 20 hours to obtain a culture liquid. Next, the culture liquid was subjected to ordinary centrifugation at 3,000 r.p.m. for 10 minutes to obtain 2 g of wet cells. These were suspended in 20 ml of 350 mM tris-hydrochloride buffer (pH 8.0) containing 25% of sucrose, and 10 mg of lysozyme (produced by Sigma Co.), 8 ml of 25 M EDTA solution (pH 8.0) and 8 ml of 20% sodium dodecylsulfate solution were added thereto. The resulting suspension was then kept at a temperature of 60° C. for 30 minutes, whereby the cells were lysed to obtain a lysate. To the lysate was added 13 ml of 5M NaCl solution, and this was treated at a temperature of 4° C. for 16 hours and then subjected to ordinary centrifugation at 15,000 r.p.m. for 30 minutes. The resulting supernatant was subjected to ordinary phenol extraction and ethanol precipitation to form a DNA precipitate.

The precipitate was dried under reduced pressure and the dried product was dissolved in 6 ml of 10 mM tris-hydrochloride buffer (pH 7.5) containing 1 mM EDTA. 6 g of cesium chloride and 0.2 ml of ethidium bromide (19 mg/ml) were added to the resulting solution, which was subjected to ordinary equilibrium density gradient centrifugation with an ultracentrifugator at 39,000 r.p.m. for 42 hours to isolate various shortened DNA fragments. In addition, after ethidium bromide was removed with n-butanol, the resulting solution was subjected to dialysis with 10 mM tris-hydrochloride buffer (pH 7.5) containing 1 mM EDTA, to obtain pure recombinant plasmids in an amount of about 500 μg.

Example 8

Analysis of Base Sequence of DNA of Containing Acetate P Gene:

Various shortened DNA fragments as obtained in Example 7 were denatured with alkali to obtain single-stranded DNA.

Figure 7:
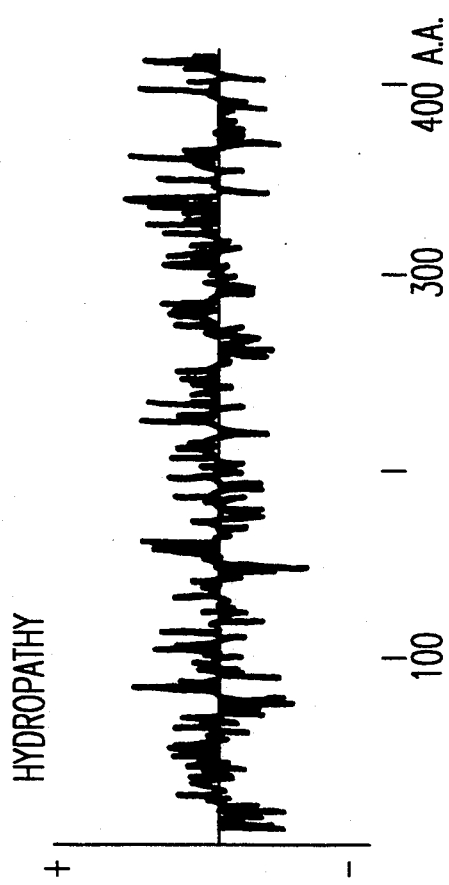
FIG. 7 shows the hydropathy plots of the translated product encoded by the acetate P gene of the present invention.

Sequencing of the resulting single-stranded DNA's was effected in accordance with the Sanger method, using M-13 sequencing kit (produced by Takara Shuzo Co.). The base sequence of the acetate P gene thus obtained is shown as SEQ ID NO: 1 in the Sequence Listing and in FIGS. 1 and 3. The amino acid sequence of the product from the gene, which is deduced from the base sequence, is also shown in SEQ ID NO:2 and 3 in the Sequence Listing and in FIGS. 2 and 3. The hydropathy plot of the gene product was determined to be one as shown in FIG. 7. As is noted therefrom, the gene product has a transmembrane domain-like structure. Therefore, the polypeptide encoded by the gene is considered to be an membrane protein, which was named acetate P, and the gene was named aceP.

As mentioned above, the present invention relates to an acetic acid assimilating gene (acetate P gene) of *E. coli*. When the gene is introduced into *E. coli* as multiple copies, the resulting *E. coli* is observed to have an elevated acetic acid assimilating capacity. Accordingly, the present invention has solved the problem of the inhibition of *E. coli* growth due to the lowering of the pH value of the culture medium in the fermentation of *E. coli*.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the united states is:

1. An isolated gene, which has a base sequence encoding a polypeptide having the amino acid sequence of SEQ ID NO:2 of the Sequence Listing.

2. The gene of claim 1, which has the base sequence of SEQ ID NO:1 of the Sequence Listing.

3. A plasmid, comprising a DNA sequence encoding a polypeptide with the amino acid sequence of SEQ ID NO: 2 of the Sequence Listing.

4. The plasmid of claim 3, wherein said DNA sequence has the base sequence of SEQ ID NO:1 of the Sequence Listing.

5. The plasmid of claim 3, which is pACEP-1.

6. A transformed bacterium of E. coli, wherein the transforming DNA sequence contains a subsequence encoding a polypeptide having the amino acid sequence of SEQ ID NO: 2 of the Sequence Listing.

7. The transformed bacterium of claim 6, wherein said DNA subsequence has the base sequence of SEQ ID NO:1 of the Sequence Listing.

8. The bacterium of claim 6, which is FERM BP-3781.

9. A method for preventing an accumulation of acetic acid in a culture medium during the culturing of a strain of Escherichia coli, comprising culturing said strain of Escherichia coli in said medium, wherein said strain of Escherichia coli has been transformed with a plasmid comprising a DNA sequence encoding a polypeptide with the amino acid sequence of SEQ ID NO:2 of the Sequence Listing.

10. The method of claim 9, wherein said plasmid comprises a DNA sequence having the base sequence of SEQ ID NO:1 of the Sequence Listing.

11. A method for preventing a reduction of the pH of a culture medium during the culturing of a strain of Escherichia coli, comprising culturing said strain of Escherichia coli in said medium, wherein said strain of Escherichia coli has been transformed with a plasmid comprising a DNA sequence encoding a polypeptide with the amino acid sequence of SEQ ID NO:2 of the Sequence Listing.

12. The method of claim 11, wherein said plasmid comprises a DNA sequence having the base sequence of SEQ ID NO:1 of the Sequence Listing.

* * * * *